United States Patent [19]

Hughes et al.

[11] 3,966,724
[45] June 29, 1976

[54] 1-(α-AMINOMETHYLBENZYL)ISOQUINO-LINE COMPOUNDS

[75] Inventors: John Lawrence Hughes, Kankakee; Jay Kenneth Seyler, Bourbonnais; Carroll M. Smith, Park Forest, all of Ill.

[73] Assignee: Armour Pharmaceutical Company, Phoenix, Ariz.

[22] Filed: Dec. 20, 1974

[21] Appl. No.: 534,741

[52] U.S. Cl. .................. 260/247.5 GP; 260/283 R; 260/288 D; 260/288 CE; 260/289 D; 424/248; 424/258
[51] Int. Cl.² ............... C07D 217/12; C07D 295/12
[58] Field of Search . 260/288 D, 288 CE, 247.5 GP

[56] References Cited
UNITED STATES PATENTS

| | | | |
|---|---|---|---|
| 3,205,233 | 9/1965 | Clarkson | 260/288 D |
| 3,362,956 | 1/1968 | Archer | 260/268 BQ |
| 3,846,432 | 11/1974 | Tanaha et al. | 260/288 D |

OTHER PUBLICATIONS

Tsatsas, Chem. Abstr., vol. 46, 11208i, (1952).
Wersbach et al., J. Med. Chem., vol. 11, pp. 760–764, (1968).

*Primary Examiner*—Nicholas S. Rizzo
*Assistant Examiner*—Mary Vaughn
*Attorney, Agent, or Firm*—Richard R. Mybeck; Carl C. Batz

[57] ABSTRACT

Compounds having the structure:

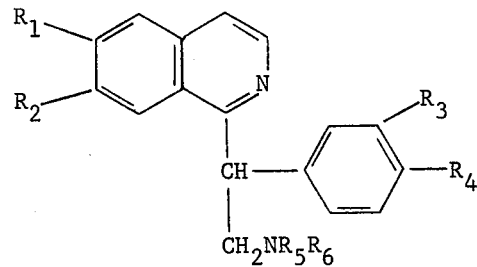

in which $R_1$ and $R_2$ are alkoxy groups of one to four carbon atoms, $R_3$ and $R_4$ each is hydrogen or an alkoxy group of one to four carbon atoms, and $R_5$ and $R_6$ each is an alkyl group of one to four carbon atoms or an arylalkyl group such as benzyl or $R_5$ taken with $R_6$ and N are pyrrolidinyl, piperidino, or morpholino groups and the pharmaceutically acceptable salts thereof and processes for preparing these compounds. These compounds are useful as vasodilators.

8 Claims, No Drawings

1-(α-AMINOMETHYLBENZYL)ISOQUINOLINE COMPOUNDS

This invention relates to 1-(α-aminomethylbenzyl)-isoquinoline compounds and to processes for the preparation of such compounds. These compounds are useful in the treatment of vasospastic conditions and peripheral vascular disease.

BACKGROUND OF THE INVENTION

A common disease, especially among elderly human patients, involves the resistance of blood vessels to the flow of blood resulting in a lowering of the amount of oxygen delivered to muscles and skin at extremities of the body such as the hands or feet and giving rise, for example, to the sensation of cold feet and intermittent claudication.

Several drugs are known which when administered to patients suffering from such vascular diseases will increase blood flow by decreasing the resistance of the blood vessels. Some of these known drugs have unwanted side effects which makes them less desirable than others.

Among the known drugs which are capable of reducing resistance to blood flow, called peripheral vasodilators, are nicotinic acid, which has the formula:

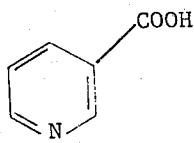

nicotinyl alcohol which has the formula:

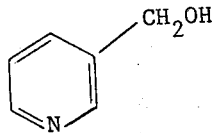

isoxsuprine which has the formula:

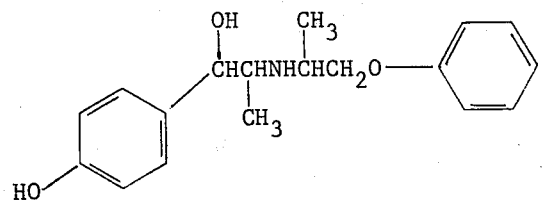

tolazoline which has the formula:

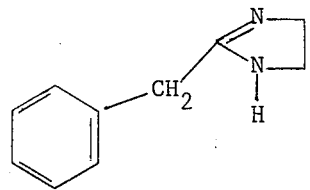

nylidrin, papaverine and cyclandelate. Of the above-named drugs, nylidrin and isoxsuprine have perhaps been more commonly administered for the relief of peripheral vascular diseases. But the search continues for vasodilator drugs which are more effective in reducing blood vessel resistance or which may have fewer side effects. Many patients who suffer from the effects of restriction to blood flow also have heart disease of some kind, and treatment with some of the known vasodilators, which also have an effect on the heart, may be too hazardous. Unwanted cardiovascular effects which have been recorded include hypertension, tachycardia, palpitations and postural hypotension. Other side effects may include headache, nausea, dizziness, nasal congestion, flushing and tingling sensations.

DESCRIPTION OF THE INVENTION

We have discovered a group of vasodilator drugs which are found to be effective for reducing vascular resistance to blood flow and which, at the same time, are relatively free of unwanted side effects. These compounds are 1-(α-aminomethylbenzyl)isoquinoline derivatives represented by the formula:

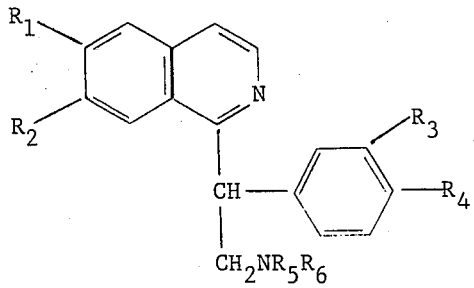

in which $R_1$ and $R_2$ are alkoxy groups of one to four carbon atoms, $R_3$ and $R_4$ each is hydrogen or an alkoxy group of one to four carbon atoms, and $R_5$ and $R_6$ each is an alkyl group of one to four carbon atoms or benzyl or $R_5$ taken with $R_6$ and N are pyrrolidinyl, piperidino, or morpholino groups and the pharmaceutically acceptable acid addition salts of said compounds.

The compounds above identified may be administered orally or parenterally in the form of their free bases or as any pharmaceutically acceptable acid addition salt of the free bases to give an effective peripheral vasodilator action.

These compounds may be prepared by heating at reflux temperature a 1-benzylisoquinoline, formaldehyde (in aqueous form or paraformaldehyde), a secondary aliphatic amine and a mineral acid, with an aliphatic alcohol as a reaction solvent. This reaction is illustrated by the following formula:

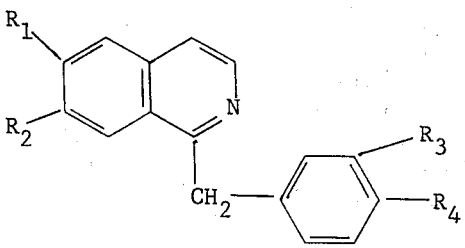

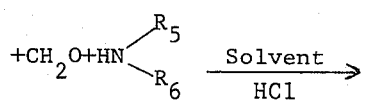

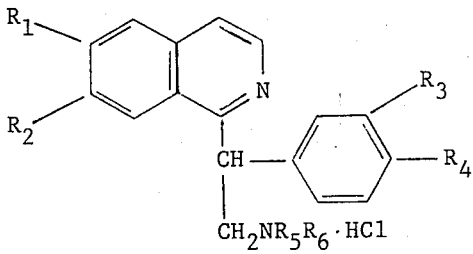

in which $R_1$ and $R_2$ are alkoxy groups of one to four carbon atoms, $R_3$ and $R_4$ each is hydrogen or an alkoxy group of one to four carbon atoms, and $R_5$ and $R_6$ each is an alkyl group of one to four carbon atoms or benzyl or $R_5$ taken with $R_6$ and N are pyrrolidinyl, piperidino, or morpholino groups and the pharmaceutically acceptable acid addition salts of said compounds.

Optimum yields can be obtained by using the reactants, the 1-benzylisoquinoline, the formaldehyde, the secondary amine and the mineral acid in molar proportions of 1.0:1.3:1.3:1.3 respectively with the solvent in at least a three molar equivalent excess. Other proportions will give the desired products at a lower efficiency.

The reacting products may be isolated from the reaction mixtures as their free bases after removal of the solvent and upon treatment with alkali metal hydroxides. The products may then be purified as their free bases or as acid addition salts.

Specific examples of processes demonstrating the preparing of our vasodilator compounds are given as follows:

EXAMPLE I

Preparation of
6,7-Dimethoxy-1-[(α-dimethylaminomethyl) veratryl] isoquinoline (P2906)

A mixture of 6.8 g (0.02 mole) of papaverine, 0.78 g (0.026 mole) of paraformaldehyde, 2.0 g (0.025 mole) of dimethylamine hydrochloride and 100 ml of ethyl alcohol were heated at reflux for 10 hours. The solvent was removed from the reaction mixture by evaporation and the residue remaining was dissolved in 100 ml of water. The solution was made basic (pH of 10) by addition of 50 percent aqueous sodium hydroxide solution and the resulting mixture extracted with two 100 ml portions of benzene. The benzene extracts were combined and washed with 100 ml of water and finally with 100 ml of aqueous saturated sodium chloride solution. The benzene layer was evaporated and the residue dissolved in 100 ml of hot cyclohexane. After filtration of the hot solution, the filtrate was cooled at 8°C for 18 hours. The precipitated solid was collected on a filter, m.p. 112°–117°C. This solid was purified by a second recrystallization from cyclohexane to yield 6.8 g melting at 119°–121°C. The infrared spectrum was consistent with the assigned structure. Analysis - Calculated for $C_{23}H_{28}N_2O_4$: C, 69.67; H, 7.12 N, 7.07. Found: C, 69.88; H, 7.18; N, 7.10.

EXAMPLE II

Preparation of
6,7-Dimethoxy-1-[(α-piperidinomethyl)-veratryl-]isoquinoline dihydrochloride (P3138)

A mixture of 10.2 g (0.03 mole) of papaverine, 1.2 g (0.04 mole) of paraformaldehyde, 4.9 g (0.04 mole) of piperidine hydrochloride and 150 ml of ethyl alcohol were heated at reflux for 7 hours. The solvent was removed from the reaction mixture by evaporation and the residue dissolved in 100 ml of water. The solution was made basic (pH of 10) by addition of 50 percent aqueous sodium hydroxide solution and the resulting mixture extracted with two 100 ml portions of benzene. The benzene extracts were combined and washed with two 100 ml portions of water and finally with 100 ml of aqueous saturated sodium chloride solution. The benzene layer was evaporated and the residue dissolved in 250 ml of acetone. The dihydrochloride salt of the product was precipitated by the addition of hydrogen chloride. This salt was collected on a filter and dried. The product melted at 175°–178°C (dec.) and weighed 15 g. This solid was recrystallized from isopropyl alcohol.

The product melted at 183°–185°C (dec.) and weighed 10.5 g. The infrared spectrum was consistent with the assigned structure. Analysis - Calculated for $C_{26}H_{34}Cl_2N_2O_4$: C, 61.28; H, 6.74; Cl, 13.92; N, 5.50; O, 12.56. Found: C, 60.88; H, 7.13; Cl, 13.79; N, 5.30; O, 12.77.

EXAMPLE III 6,7-Dimethoxy-1-[α-(N-methyl-N-benzyl-)aminomethyl] veratrylisoquinoline (P2984)

A mixture of 37.6 g (0.1 mole) of papaverine hydrochloride, 3.9 g (0.13 mole) of paraformaldehyde, 15.1 g (0.125 mole) of N-methyl benzylamine, 2.03 ml of concentrated hydrochloric acid and 500 ml of ethyl alcohol were stirred and heated at reflux for 9 hours. The solvent was removed from the reaction mixture by evaporation, leaving a viscous residue which was dissolved in 200 ml of water. This solution was made basic by addition of aqueous 10N sodium hydroxide solution. This solution was extracted with three 100 ml portions of benzene. The combined benzene extracts were washed with 200 ml of water and dried over anhydrous magnesium sulfate. The mixture was filtered and the benzene was removed by evaporation. The residue was dissolved in 150 ml of a 5:1 mixture of cyclohexane and benzene. This solution was kept at 25°C for 72 hours. The precipitated solid which was identified as papaverine was removed by filtration. This material weighed 8.0 g. The filtrate was then diluted with 150 ml of cyclohexane and stored at 0°C for 96 hours. The precipitated solid was collected on a filter and recrystallized twice from aqueous 75% methanol. The white crystalline product weighing 27.0 g melted at 95°–97°C. The infrared spectrum was consistent with the assigned structure. Analysis - Calculated for $C_{29}H_{32}N_2O_4$: C, 73.70; H, 6.83; N, 5.93; O, 13.54. Found: C, 73.83; H, 6.94; N, 5.94; O, 13.27.

EXAMPLE IV 6,7-Dimethoxy-1-(α-morpholinomethyl)-veratrylisoquinoline dihydrochloride (P3313)

A mixture of 8 g (0.024 mole) of papaverine, 0.93 g (0.031 mole) of paraformaldehyde, 2.62 g (0.030 mole) of morpholine, 2.5 ml of concentrated hydrochloric acid, and 100 ml of ethyl alcohol was stirred and heated at reflux for 8 hours. The reaction mixture was cooled at −5°C for 24 hours. The cooled reaction mixture was filtered to remove 1.5 g of papaverine hydrochloride. The filtrate was evaporated to a thick residue. This was dissolved in 100 ml of water and the solution made basic by the addition of 10N sodium hydroxide solution. The basic mixture was extracted with three 100 ml portions of ether. The ether extracts were combined, dried over anhydrous magnesium sulfate and filtered. The product was precipitated from the ether solution by the addition of hydrogen chloride. The precipitated solid was collected on a filter and recrystallized twice from isopropyl alcohol to yield 4.0 g of product melting at 182°–184°C. The infrared spectrum was consistent with the assigned structure. Analysis - Calculated for $C_{25}H_{32}Cl_2N_2O_5$: C, 58.70; H, 6.32; Cl, 13.86; N, 5.48. Found: C, 58.91; H, 6.30; Cl, 13.37; N, 5.34.

EXAMPLE V 6,7-Dimethoxy-1-(α-di-n-butylaminomethyl)veratrylisoquinoline dihydrochloride (P3202)

A mixture of 10.2 g (0.03 mole) of papaverine, 1.2 g (0.04 mole) of paraformaldehyde, 5.12 g (0.04 mole) of di-n-butylamine, 3.3 ml of concentrated hydrochloric acid and 150 ml of ethyl alcohol was stirred and heated at reflux for 7 hours. The reaction mixture was cooled at −5°C for 24 hours and the precipitated papaverine hydrochloride removed by filtration. The filtrate was evaporated to a viscous oil and this residue product dissolved in 150 ml of water. The aqueous solution was made basic by the addition of 10N sodium hydroxide solution. The resulting mixture was extracted with two 100 ml portions of benzene. The benzene solution was reduced to a volume of 50 ml and the solution placed on a alumina chromatography column. The column was eluted with isopropyl alcohol. The purified product was converted to a dihydrochloride salt. This salt was further purified by recrystallization from a 1:1 mixture of acetone and ether. The white crystaline product weighed 5.0 g and melted at 137°–141°C. The infrared spectrum was consistent with the assigned structure. Analysis - Calculated for $C_{29}H_{42}Cl_2N_2O_4$: C, 62.91; H, 7.66; N, 5.06. Found: C, 62.83; H, 7.70; N, 5.01.

EXAMPLE VI 6,7-Dimethoxy-1-[α-(N-methyl-N-benzylamino)-methyl] benzylisoquinoline (P 3274)

A mixture of 15.08 g (0.05 mole) of 1-benzyl-6,7-dimethoxyisoquinoline hydrochloride, 2.3 g (0.075 mole) of paraformaldehyde, 8.1 g (0.067 mole) of N-methylbenzylamine, 1.5 ml of concentrated hydrochloric acid and 150 ml of ethyl alcohol was stirred and heated at reflux for 8 hours. The reaction mixture was evaporated to a viscous oil. This oil was dissolved in 100 ml of water. The aqueous solution was washed with 100 ml of ether. The aqueous layer was made basic by addition of 10N sodium hydroxide solution. The mixture was extracted with two 100 ml portions of ether. The ether extracts were combined and dried over anhydrous magnesium sulfate. The ether solution was filtered and evaporated. The residue was dissolved in 25 ml of cyclohexane and placed on an alumina chromatography column. The column was eluted with a 1:9 mixture of ether and cyclohexane. The product obtained from the column was further purified by recrystallization from hexane. The crystalline product melted at 82°–84°C and weighed 4.0 g. The infrared spectrum was consistent with the assigned structure. Analysis - Calculated for $C_{27}H_{28}N_2O_2$: C, 78.62; H, 6.84; N, 6.79. Found: C, 78.64; H, 6.92; N, 6.68.

To demonstrate effectiveness of the compounds prepared in the foregoing specific Examples I to VI, each of these compounds were administered intra-arterially in the carotid artery perfused with blood at a constant rate of an anesthetized dog. In order to compare these compounds with a known vasodilator, papaverine hydrochloride was administered under the same conditions. The compounds were compared both with respect to vasodilator response and as to tachycardia response, and the data is recorded in Table I.

TABLE I

Comparison of Vasodilator and Tachycardia Responses with Papaverine Hydrochloride

| Compound | Vasodilator Response | Heart rate Response |
|---|---|---|
| Papaverine Hydrochloride | 100% | 3 |
| P-2906 | 75% | 0 |
| P-2984 | 80% | 0 |
| P-3113 | 96% | 1 |
| P-3138 | 23% | 0 |
| P-3202 | 24% | 0 |

TABLE I-continued

| | Comparison of Vasodilator and Tachycardia Responses with Papaverine Hydrochloride | |
|---|---|---|
| Compound | Vasodilator Response | Heart rate Response |
| P-3274 | 28% | 0 |

The vasodilator response values given in Table I represent percent difference between the average drop in pressure caused by the intra-arterial administration of an agent into the carotid artery, and the tachycardia response values are based upon the percent increase in the heart rate after administration of 1 mg/kg body weight of the dog. Heart rate increases of 0–6% are rated 0; 6 to 13% as 1; 14 to 20% as 2; and over 20% as 3.

While only certain embodiments of our invention have been described and demonstrated in detail, it is understood that the invention may take many and various forms and is subject to wide variation all within the spirit of the invention and the scope of the following claims.

We claim:
1. A compound having the structure:

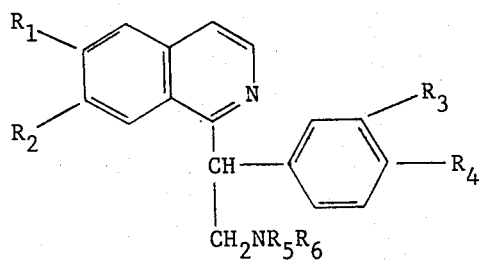

in which $R_1$ and $R_2$ are alkoxy groups of one to four carbon atoms, $R_3$ and $R_4$ each is hydrogen or an alkoxy group of one to four carbon atoms, and $R_5$ and $R_6$ each is an alkyl group of one to four carbon atoms or benzyl or $R_5$ taken with $R_6$ and N are pyrrolidinyl, piperidino, or morpholino groups and the pharmaceutically acceptable salts thereof.

2. A compound having the structure:

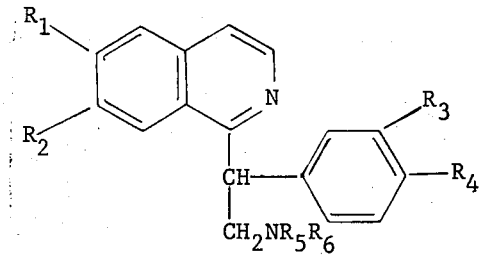

in which $R_1$ and $R_2$ are alkoxy groups of one to four carbon atoms, $R_3$ and $R_4$ each is hydrogen or an alkoxy group of one to four carbon atoms, and $R_5$ and $R_6$ each is an alkyl group of one to four carbon atoms or a benzyl group.

3. The compound of claim 1 in which
   $R_1$, $R_2$, $R_3$ and $R_4$ each is a methoxy group and
   $R_5$ and $R_6$ each is a methyl group.

4. The compound of claim 1 in which
   $R_1$, $R_2$, $R_3$ and $R_4$ each is a methoxy group and
   $R_5$ and $R_6$ taken together with N is a piperidino group.

5. The compound of claim 1 in which
   $R_1$, $R_2$, $R_3$ and $R_4$ each is a methoxy group,
   $R_5$ is a methyl group and
   $R_6$ is a benzyl group.

6. The compound of claim 1 in which
   $R_1$, $R_2$, $R_3$ and $R_4$ each is a methoxy group and
   $R_5$ and $R_6$ taken together with N is a morpholino group.

7. The compound of claim 1 in which
   $R_1$, $R_2$, $R_3$ and $R_4$ each is a methoxy group and
   $R_5$ and $R_6$ each is an n-butyl group.

8. The compound of claim 1 in which
   $R_1$ and $R_2$ each is a methoxy group,
   $R_3$ and $R_4$ each is hydrogen,
   $R_5$ is a methyl group and
   $R_6$ is a benzyl group.

* * * * *